United States Patent [19]

Prasad et al.

[11] 3,971,849

[45] July 27, 1976

[54] 1,N⁶-ETHENO-5'-ADENOSINE CARBOXYLATES FOR INCREASING CORONARY SINUS PARTIAL PRESSURE OF OXYGEN

[75] Inventors: Raj Nandan Prasad, Pierrefonds; David Lyon Garmaise, Montreal, both of Canada

[73] Assignee: Abbott Laboratories, North Chicago, Ill.

[22] Filed: May 21, 1974

[21] Appl. No.: 471,940

Related U.S. Application Data

[62] Division of Ser. No. 317,325, Dec. 21, 1972, Pat. No. 3,830,795.

[52] U.S. Cl. ............................................. 424/180
[51] Int. Cl.² .......................................... A61V 31/70
[58] Field of Search ................................. 424/180

*Primary Examiner*—Jerome D. Goldberg
*Attorney, Agent, or Firm*—Robert L. Niblack; Vincent A. Mallare

[57] ABSTRACT

Esters of 1,N⁶-etheno-5'-adenosine carboxylic acid represented by the formula

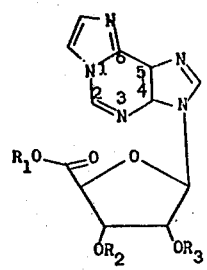

wherein $R_1$ is loweralkyl, loweralkenyl, loweralkynyl or cycloalkyl; and $R_2$ and $R_3$ each are hydrogen or acyl, or $R_2$ and $R_3$ taken together form an isopropylidene or benzylidene moiety; and the pharmaceutically acceptable acid addition salts thereof.

The compounds wherein $R_2$ and $R_3$ are hydrogen are useful in treating cardiovascular disorders and are particularly useful as anti-anginal and anti-hypertensive agents. Compounds wherein $R_2$ and $R_3$ are acyl or when taken together form an isopropylidene or benzylidene moiety are intermediates useful in the preparation of the final products. ($R_2$ and $R_3$ = hydrogen). The final products are also useful as intermediates for preparing pharmaceutically active compounds, and, more specifically, for preparing the corresponding 1,N⁶-etheno-5'-adenosine carboxamides.

2 Claims, No Drawings

1,N⁶-ETHENO-5'-ADENOSINE CARBOXYLATES FOR INCREASING CORONARY SINUS PARTIAL PRESSURE OF OXYGEN

This is a division, of application Ser. No. 317,325 filed Dec. 21, 1972, now U.S. Pat. No. 3,830,795 issued Aug. 20, 1974.

DETAILED DESCRIPTION OF THE INVENTION

This invention relates to novel nucleosides, and more particularly relates to 1,N⁶-etheno-5'-adenosine carboxylates.

The compounds of this invention are represented by the formula

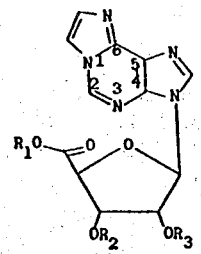

wherein $R_1$ is loweralkyl, loweralkenyl, loweralkynyl or cycloalkyl; and $R_2$ and $R_3$ each are hydrogen or acyl, or $R_2$ and $R_3$ taken together form an isopropylidene or benzylidene moiety; and the pharmaceutically acceptable acid addition salts thereof.

The compounds wherein $R_2$ and $R_3$ are hydrogen are useful in treating cardiovascular disorders and are particularly useful as anti-anginal and anti-hypertensive agents. Compounds wherein $R_2$ and $R_3$ are acyl or when taken together form an isopropylidene or benzylidene moiety are intermediates useful in the preparation of the final products. The final products are also useful as intermediates for producing pharmaceutically active compounds and more specifically, are useful in producing the corresponding amides which are useful as anti-anginal and anti-hypertensive agents.

The term "loweralkyl," as used herein, refers to both straight and branched alkyl radicals containing from 1 to 6 carbon atoms, including methyl, ethyl, n-propyl, iso-propyl, n-butyl, sec-butyl, tert-butyl, iso-butyl, n-pentyl, iso-pentyl, neo-pentyl, n-hexyl and the like.

"Loweralkenyl" refers to the $C_2$ to $C_5$ alkyl groups, as defined above, from which a hydrogen atom has been removed from each of two adjacent carbon atoms to produce ethylenic unsaturation; e.g., vinyl, allyl, methallyl, 1-pententyl and the like.

"Loweralkynyl" refers to the $C_2$ to $C_5$ alkyl groups as defined above, from which 2 hydrogen atoms have been removed from each of two adjacent carbon atoms to produce acetylenic unsaturation such as ethynyl, propargyl, 2-butynyl, 1-pentynyl and the like.

The term "cycloalkyl" refers to $C_3$-$C_6$ cycloalkyl groups, namely, cyclopropyl, cyclopropylmethyl, cyclobutyl, cyclopentyl and cyclohexyl.

The term "pharmaceutically acceptable acid addition salts" refers to non-toxic salts prepared by reacting the ester with the appropriate organic or inorganic acid, or by utilizing an acid addition salt of the appropriate intermediate. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

The term "acyl" refers to acetyl, propionyl, butyryl and the like.

The compounds of this invention are useful as anti-anginal agents at dosages of from 0.1 to 100 mg./kg. of body weight daily.

The anti-anginal activity was first established by measuring the increase in coronary sinus partial pressure of oxygen ($pO_2$) according to the method of Schoepke et al., *Pharmacologist* 8; 204, (1966).

Generally speaking, the compounds of this invention are prepared by reacting adenosine-5'-carboxylic acid prepared from 2',3'-isopropylidene adenosine, according to the method described by Harmon et al., *Chem. Ind.* 1969, (1141) with an appropriate dry alcohol in the presence of an acid catalyst like thionylchloride to obtain the ester. The ester is then reacted with chloroacetaldehyde according to the following reaction scheme to obtain the etheno compounds of this invention:

Reaction Scheme

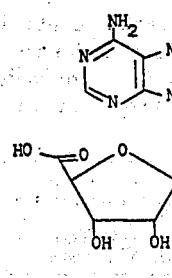 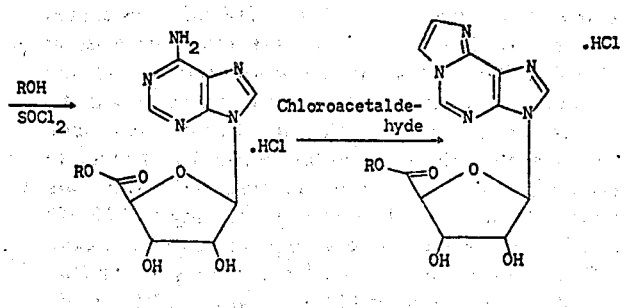

The following examples further illustrate this invention:

EXAMPLE 1

Adenosine-5'-Carboxylic Acid, Ethyl Ester 11.7 g. of Isopropylidene adenosine were dissolved in 3.5 liters of water and the pH was adjusted to 12.2 by the addition of 5.85 g. of potassium hydroxide. 23.7 g. of potassium permanganate in 825 ml. of water were added dropwise with stirring over a period of 3¾ hours.

The solution was then allowed to sit at room temperature overnight. The excess permanganate was destroyed by the dropwise addition of 30% hydrogen peroxide and the reaction mixture was filtered through a layer of $NH_3$-washed celite. The yellow filtrate was concentrated in vacuo at 35°–45° to 600 ml. and the acid precipitated in an ice bath by adjusting the pH to 4.5 by the dropwise addition of 1:3 HCl. The white precipitate was washed with dilute (1:1000) acetic acid and dried at 135°C. to yield 7.93 g. of the crude isopropylidene product, m.p. 265–8°. The material was taken up in 100 ml. of dilute $NH_3$, and recrystallized by adjusting the pH to 4.5 by the addition of 1:3 acetic acid to yield 7.7 g. of 2',3'-isopropylidene adenosine-5'-carboxylic acid, m.p. 272–3°.

Analysis Calcd. for $C_{13}H_{15}N_5O_5$: C, 47.89; H, 4.65; N, 21.59; O, 25.03. Found: C, 48.60; H, 4.71; N, 21.80; O, 24.90.

EXAMPLE 2

Ethyl (1,N⁶-Etheno)Adenosine-5'-Carboxylate Monohydrochloride

A suspension of ethyl adenosine-5'-carboxylate (4.0 g; 0.013 mole) in water (70 ml.) containing chloroacetaldehyde (40 ml. of a 30% aqueous solution) and a few drops of glacial acetic acid was stirred at 50°C. for 18 hours.

At the end of this period the reaction mixture was evaporated to dryness under reduced pressure. The residue was recrystallized from absolute ethanol to give the analytically pure ethyl (1,N⁶-etheno)adenosine-5'-carboxylate monohydrochloride containing one mole of ethanol, melting at 128–30° dec; $R_f$ 0.47 (solvent system: n-butanol/water = 43/7).

Anal. Calcd. for $C_{14}H_{15}N_3O_5 \cdot HCl \cdot EtOH$; C, 46.21; H, 5.33; N, 16.84. Found; C, 45.74; H, 5.22; N, 17.25.

The ethyl adenosine-5'-carboxylate hydrochloride required was prepared by the following method:

A suspension of adenosine-5'-carboxylic acid (5.62 g; 0.02 mole) in absolute ethanol (300 ml.) was cooled and thionyl chloride (6.0 ml.) was added dropwise at 0°–10°C. The reaction mixture was stirred for 16 hours at room temperature. At the end of this period the mixture was cooled to −10°C. and filtered. The residue was washed with cold absolute ethanol and ether to give 6.7 g. (97%) of ethyl adenosine-5'-carboxylate hydrochloride as a white powder, melting at 171–72° dec. This sample was pure enough for further reaction.

Recrystallization from absolute ethanol gave the analytical sample melting at 174° dec.; $[\alpha]_D^{26}$ −22°C ± 0.55° (C = 1.8 in $H_2O$).

Anal. Calcd. for $C_{12}H_{15}N_5O_5 \cdot HCl$ (345.5); C, 41.67; H, 4.63; Cl, 10.27; N, 20.26. Found: C, 41.91; H, 4.91; Cl, 10.07; N, 19.81.

The free base (ethyl adenosine-5'-carboxylate) was obtained by treating the aqueous solution of the hydrochloride with a $NaHCO_3$ solution at 5°C.

EXAMPLE 3

1,N⁶-Etheno adenosine-5'-carboxylic acid, allyl ester is prepared according to the method of Example 2 from adenosine-5'-carboxylic acid, allyl ester and chloroacetaldehyde.

EXAMPLE 4

1,N⁶-Etheno adenosine-5'-carboxylic acid, n-butyl ester is prepared according to the method of Example 2 from adenosine-5'-carboxylic acid, n-butyl ester.

EXAMPLE 5

1,N⁶-Etheno adenosine-5'-carboxylic acid, iso-propyl ester is prepared according to the method of Example 2 from adenosine-5'-carboxylic acid, iso-propyl ester and chloroacetaldehyde.

EXAMPLE 6

1,N⁶-Etheno adenosine-5'-carboxylic acid, propargyl ester is prepared according to the method of Example 2 from adenosine-5'-carboxylic acid propargyl ester and chloroacetaldehyde.

EXAMPLE 7

1,N⁶-Etheno adenosine-5'-carboxylic acid, n-pentyl ester is prepared according to the method of Example 2 from adenosine-5'-carboxylic acid, n-pentyl ester and chloroacetaldehyde.

EXAMPLE 8

1,N⁶-Etheno adenosine-5'-carboxylic acid, methallyl ester is prepared according to the method of Example 2 from adenosine-5'-carboxylic acid methallyl ester and chloroacetaldehyde.

EXAMPLE 9

1,N⁶-Etheno adenosine-5'-carboxylic acid, 1-pentynyl ester is prepared according to the method of Example 2 from adenosine-5'-carboxylic acid, 1-pentynyl ester and chloroacetaldehyde.

EXAMPLE 10

1,N⁶-Etheno adenosine-5'-carboxylic acid, cyclopentyl ester is prepared according to the method of Example 2 from adenosine-5'-carboxylic acid, cyclopentyl ester and chloroacetaldehyde.

EXAMPLE 11

Tablets containing 25 mg. of 1,N⁶-Etheno adenosine-5'-carboxylic acid and having the following composition are prepared according to methods well known in the art.

| | |
|---|---|
| 1,N⁶-Etheno adenosine-5'-carboxylic acid, ethyl ester hydrochloride | 10 mg. |
| Starch | 10 mg. |
| Colloidal silica | 3 mg. |
| Magnesium stearate | 2 mg. |

The compounds of this invention can be formulated into various pharmaceutical dosage forms such as tablets, capsules, pills, and the like, for immediate or sustained release, by combining the active compound with a suitable pharmaceutically acceptable carrier or diluent according to methods well known in the art. Such dosage forms may additionally include excipients, binders, fillers, flavoring and sweetening agents and other therapeutically inert ingredients necessary in the formulation of the desired pharmaceutical preparation.

We claim:

1. A method of increasing coronary sinus partial pressure of oxygen in a patient in need of such treatment comprising administering an effective coronary sinus partial pressure of oxygen increasing amount of a compound of the formula

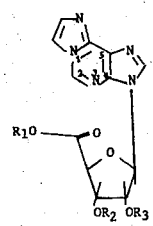

wherein $R_1$ is loweralkyl, loweralkenyl, loweralkynl or cycloalkyl of 3 to 6 carbon atoms; and $R_2$ and $R_3$ each are hydrogen, acetyl, propionyl or butyryl, or $R_2$ and $R_3$ taken together form isopropylidene or benzylidene; or the pharmaceutically acceptable acid addition salts thereof to said patient.

2. A method according to claim 1 wherein a pharmaceutical composition is administered which comprises said compound and a pharmaceutical acceptable inert carrier or diluent.

* * * * *